United States Patent [19]
Lustig et al.

[11] Patent Number: 5,142,723
[45] Date of Patent: Sep. 1, 1992

[54] TOOTH CLEANING APPARATUS HAVING POWERED BRUSH AND SPRAY

[75] Inventors: L. Paul Lustig, 304 Greenwood St., Newton, Mass. 02159; Andrew Tybinkowski, Boxford, Mass.

[73] Assignee: L. Paul Lustig, Newton Centre, Mass.

[21] Appl. No.: 611,898

[22] Filed: Nov. 9, 1990

[51] Int. Cl.$^5$ .................. A61C 17/36; B08B 13/04
[52] U.S. Cl. ........................... 15/22.1; 15/28; 128/62 A; 128/66
[58] Field of Search .................. 15/22.1, 28; 433/80–82, 131, 216, 125; 128/62 A, 66

[56] References Cited

U.S. PATENT DOCUMENTS

| | | | |
|---|---|---|---|
| 3,480,981 | 12/1969 | Murov et al. | 15/22.1 |
| 3,536,965 | 10/1970 | Moret et al. | 15/22.1 |
| 4,146,020 | 3/1979 | Moret et al. | 15/22.1 |
| 4,282,867 | 8/1981 | DuToit | 128/66 |
| 4,365,376 | 12/1982 | Oda et al. | 15/22.1 |
| 4,845,795 | 7/1989 | Crawford et al. | 15/22.1 |

*Primary Examiner*—Edward L. Roberts
*Attorney, Agent, or Firm*—Lahive & Cockfield

[57] ABSTRACT

A dental hygiene (10) has a housing (12) that provides a manually deployable handle for the device and that houses a motor (14) that drives both a brush agitating drive mechanism (16) and a liquid dispensing pump mechanism (18). The housing (12) has a tool mount (20) that interchangably mounts in operable relation with the drive mechanism and with the pump mechanism any one of a dental brush tool (22) and a dental spray tool (24). The brush tool and the drive mechanism preferably are arranged to agitatingly drive two sets of brush elements (26) and (28) oppositely, preferably with back and forth rotation of individual brush tufts.

5 Claims, 3 Drawing Sheets

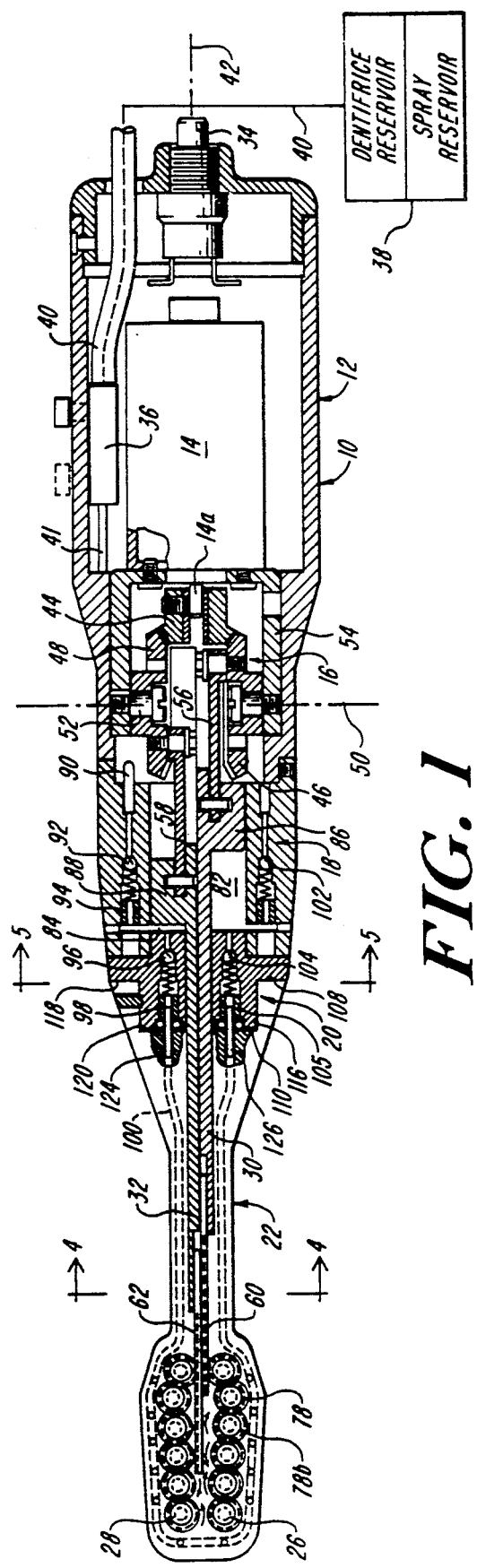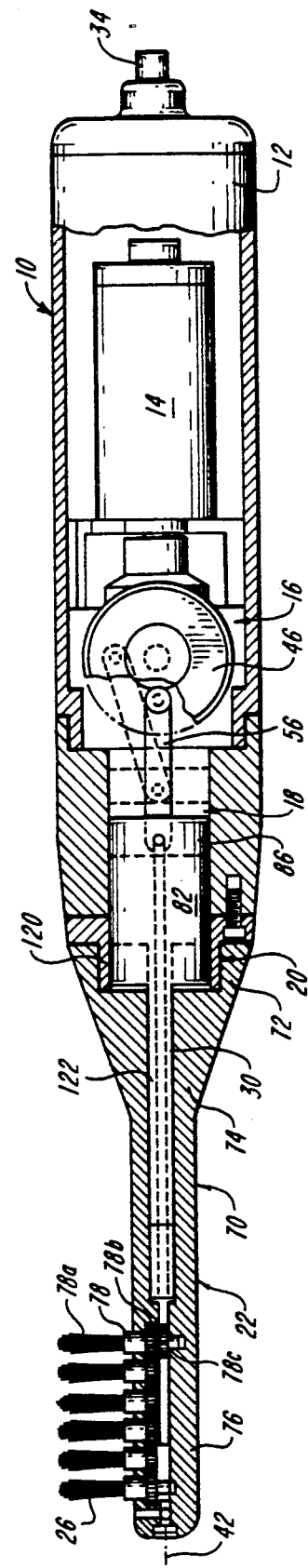

TOOTH CLEANING APPARATUS HAVING POWERED BRUSH AND SPRAY

BACKGROUND

This invention relates to dental hygiene devices. In particular, this invention provides an appliance for cleaning teeth both with brushing action and with liquid spray or jet action. The brush loosens plaque from tooth surfaces and the jet flushes away the plaque debris. The appliance also provides gingival stimulation and enhances the peripheral capillary dental circulation.

Conventional hand brushing dental hygiene practices are fairly efficient for cleaning smooth facial and lingual surfaces of the teeth because the bristle tips of a conventional toothbrush can readily access these broad surfaces. However, major incidences of tooth decay and of periodontal disease occur in interproximal areas such as crevices between adjacent teeth and the pits and fissures of the occlusal surfaces. Cleaning these areas with traditional hand brushing methods generally is unsatisfactory, with ineffective removal of residue and of dental plaque, and resulting in increased susceptibility to tooth decay and periodontal disease.

Among the prior techniques proposed to solve these problems are powered brushes, in which the entire brush head is moved while water or another fluid is emitted from the brush head. Other prior art techniques are powered brushes in which the brush head has rotating tufts of bristles, and liquid jet devices.

Powered brushes in the first category, such as disclosed in U.S. Pat. No. 3,178,754 issued to Cleverdon, have a brush structure similar to that of a hand brush, augmented by the delivery of a stream of liquid between the brush bristles. The fluid flow is intended to increase the cleaning effect of the brush and provide cleaning in crevices the brush cannot reach. However, the powered brushes suffer disadvantages similar to a hand brush.

Powered toothbrush apparatus of the second category, as disclosed in U.S. Pat. No. 4,845,795 issued to Crawford et al., and U.S. Pat. No. 4,156,620 issued to Clemens, commonly rotate individual tufts of the brush head. This type of toothbrush apparatus can be further divided into those in which the tufts are continuously rotated in one direction, and those in which the tufts rotate in one direction and then rotate in the other direction. Brushes in which tuft rotation is unidirectional tend to move out of crevices between large surfaces of teeth. The prior brushes in which the tufts alternate direction of rotation, i.e. with bidirectionally rotatable tufts, are limited to cleaning those surfaces of the teeth that are accessible to the bristles.

An alternative method of dental hygiene is the use of liquid jet devices, such as disclosed in U.S. Pat. No. 3,800,786 issued to Kovach. These devices draw fluid from a reservoir and direct a fine, high-velocity jet at the dental area to be cleaned. By applying varying amounts of pressure, a liquid jet can also be used for massaging the gums. While a liquid jet is useful for cleaning small spaces that cannot be reached with a brush, it is not as efficient as a brush for cleaning large dental surfaces.

It accordingly is an object of this invention to provide a multiple-functioning dental hygiene apparatus for facilitating cleaning teeth with both a brushing action and with a jet spray action. It is a further object that the apparatus optionally provide a localized direct liquid application with the brushing action.

It is also an object of the invention to provide a multiple-functioning dental hygiene appliance of the above character that can deliver liquid dentifrice during cleaning with brush action and alternatively can deliver a cleaning liquid with the spray action.

A further object of the invention is to provide an oral hygiene device of the above character that has a relatively simple mechanism, that can be manufactured at a relatively low cost, and that can be compact and easy to use.

Other objects of the invention will in part be obvious and will in part appear hereinafter.

SUMMARY OF THE INVENTION

A dental appliance in accordance with the invention has a housing that serves as, the appliance handle that contains a power element that includes a motor and an associated drive mechanism. The handle has a tool mount that replaceably and removably mounts a dental tool operably connected with the motor element, for selectively powering and displaying the mounted dental tool. The appliance further has a dental brush tool that has an agitatable brush element, one form of which is a multiplicity of brush tufts each of which is mounted for driven rotation. The brush tool has a tool mount that mates removably and replaceably with the tool mount on the housing handle for both mounting the brush tool with the housing and for placing the brush tool in operable communication with the motor element, for example for agitating the brush elements by way of the motor element. In one preferred embodiment the motor element rotates two subsets of the brush tufts in opposite directions, and, further, alternates the rotation directions of the brush elements.

The mount of the brush tool in addition couples through the mount on the housing with a pump mechanism, of the power element to dispense dentifrice or other liquid from the brush tool to the dental site being brushed.

The appliance further has a second tool namely a dental spray tool, that has a liquid nozzle. The dental spray tool has a tool mount that mates removably and replaceably with the tool mount of the housing for mounting the spray tool operably with the housing. The mounting of the dental spray tool with the housing handle, which is alternative to the mounting of the dental brush tool, in addition places the spray nozzle in operable communication with the pump mechanism, for the selective delivery of a pressured liquid to the nozzle. Secondly, when fitted with the spray element, the appliance can discharge a cleaning or other dental hygiene liquid by way of the spray tool and by using the same drive and pump mechanism that, alternatively, drives the dental brush tool when the latter is fitted to the tool housing. The power element of the dental appliance thus has an actuating element for actuating the brush element of a dental brush tool mounted thereon and has an element for controlling or otherwise effecting the delivery or liquid to the mounted brush tool and, alternatively, to the mounted spray tool.

It is also a feature of the dental appliance according to the invention that the interfitting tool mounts, both on the housing and on each dental tool, provide both mechanical tool support and coupling of liquid from the pump element to which ever dental tool is in use.

According to another feature of the invention, it provides a dental appliance that has a manually deployable housing that can mount a dental tool and for the delivery of liquid for discharge from that dental tool. The appliance has a liquid-driving pump mounted with the manually deployable housing. In one preferred form, the pump has at least one pump chamber slidably fitted with a piston for the delivery of pumped liquid to whatever dental tool is mounted on the housing. A motor element mounted with the manually deployable housing is operatively coupled with the pump for drivingly pumpingly moving the pump piston relative to the pump chamber.

This dental appliance also features a liquid port for receiving liquid and an input valve element for controlling the delivery of liquid from the input port to the pump chamber, and, further, has an output valve element for controlling the delivery of the pumped liquid from the chamber for application to the dental tool.

A dental appliance in accordance with another feature of the invention has a manually deployable housing that mounts a motor element for providing a reciprocating drive to agitatingly drive brush elements of a dental brush tool and, further, has an improvement wherein two side-by-side reciprocating members are coupled with the motor element for receiving out of phase reciprocating motion to provide the reciprocating drive to actuate the brush elements. A dental appliance in accordance with this feature of the invention further has a liquid pump element mounted within the housing and having at least two pump chambers, each slidably fitted with a pumping piston, and having valved fluid passages for the delivery of liquid to the chambers and for the further delivery of pumped liquid from the chambers for application for a dental tool that is coupled to the housing. The appliance features a common drive mechanism for both the pumping elements and the reciprocating elements. More particularly, it has mechanical drive elements operatively connecting a pump element with a motor element, for providing reciprocation of the piston elements relative to the pump chamber elements. This feature of the invention provides a driving reciprocation both of the pump and of the brush-agitating reciprocating elements in common by the motor.

One preferred brush tool has two sets of brush elements, each rotatably mounted with the tool. The appliance further has two first reciprocating member that engage the two sets of brush elements, for agitatingly driving them in opposite direction. The reciprocation members can repeatedly engage with, and disengage from, the brush elements to allow the interchange of the dental tool.

One consumer product in accordance with the invention provides a single hand-held motorized drive handle to which either a brushing tool or a jet spraying tool can be coupled. With the brushing tool fitted to the powered handle, the handle power element rotates two sets of brushing elements on the tool in opposite directions and reverses the brushing directions, thereby maximizing the brushing cleaning action. Further, the motorized handle contains a pump for delivering a liquid dentifrice for discharge through the brush tool, to enhance the brushing cleaning with a liquid dentifrice.

This consumer product in addition fits a spray tool to the motorized handle, in place of the brush tool, with a relatively simple yet secure interchange operation. With the spray tool fitted to the motorized handle, the motor element in the handle provides a spraying discharge of selected cleaning or other liquid to the dental site at which the spray tool is directed. The invention thus enables a user to attain multiple dental hygienic cleaning operations with a single motorized tool handle that replaceably fits at least two tool elements, each of which can operate with the discharge with a selected liquid, all with operator control.

The invention accordingly comprises the features of construction, combinations of elements and arrangement of parts exemplified in the construction hereinafter set forth, and the scope of the invention is indicated in the claims. For a fuller understanding of the nature and objects of the invention, reference is to be made to the following detailed description and the accompanying drawings, in which FIG. 1 is a longitudinal view, partly in section of a dental appliance in accordance with the invention and fitted with a dental brush tool;

FIG. 2 is a longitudinal view, partly in section, of the dental appliance and brush tool of FIG. 1 rotated 90° from the plane of FIG. 1;

Figure 3:
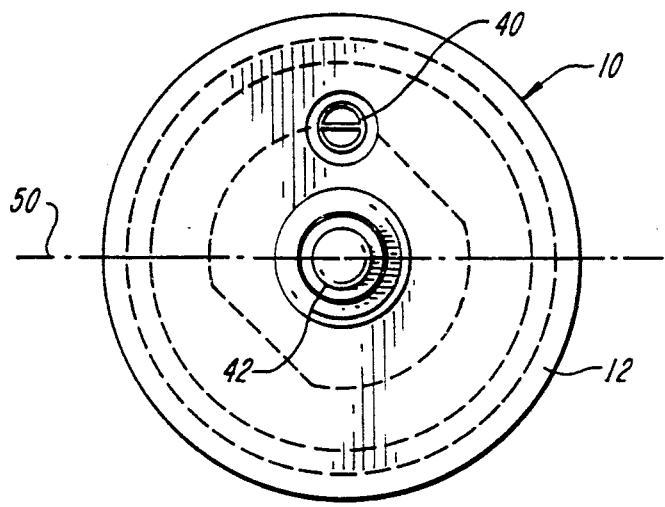
FIG. 3 is a end elevation view of the dental tool of FIG. 1.
Figure 4:
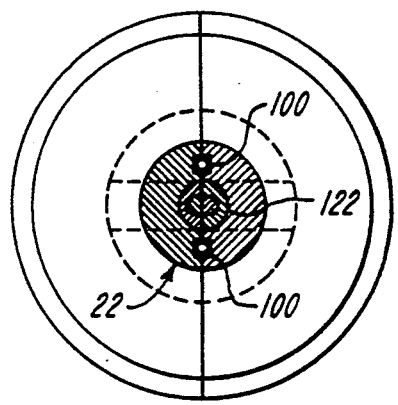
Figure 5:
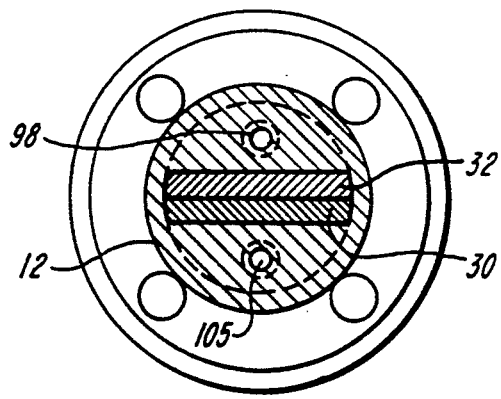
Figure 6:
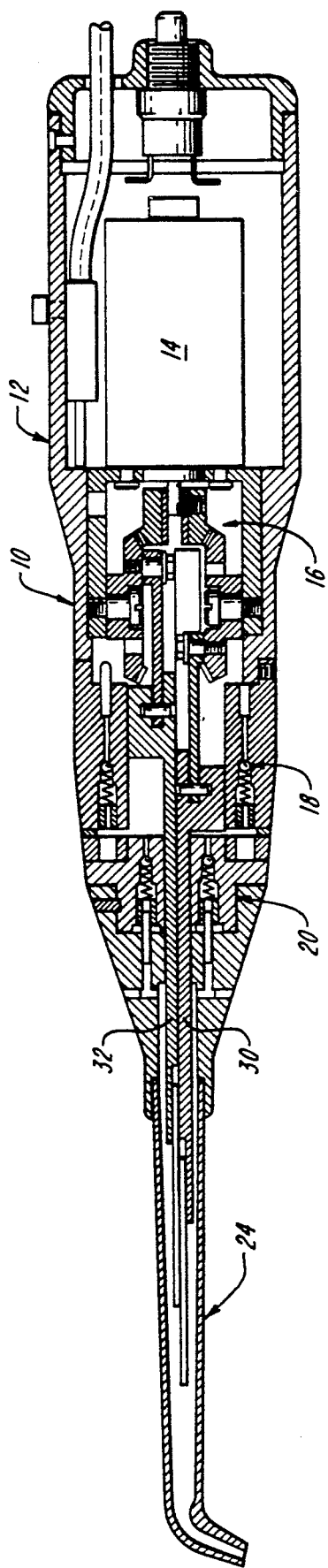
Figure 7:
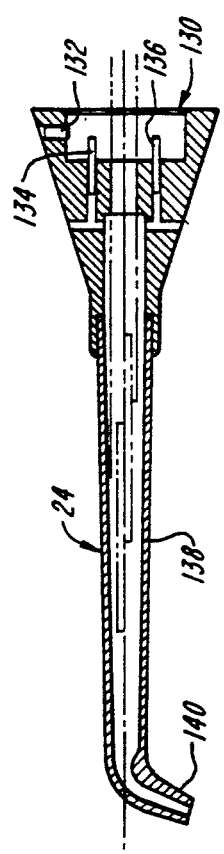

FIGS. 4 and 5 are transverse sectional views of the tool of FIG. 1 taken along section lines 4—4 and 5—5, respectively;

FIG. 6 is a view similar to FIG. 1, showing the appliance fitted with a dental spray tool; and FIG. 7 is a longitudinal view, partly broken away, of the dental spray tool FIG. 6.

DESCRIPTION OF ILLUSTRATED EMBODIMENTS

A dental hygiene appliance 10 in accordance with the invention has, as shown in FIGS. 1 and 2, a housing 12 that contains a motor 14, a reciprocating drive mechanism 16 and a pump mechanism 18. The housing, which serves as a handle for the manually deployable appliance, has a tool mount 20 at one axial end and which mounts a dental brush tool 22 to the housing. The brush tool 22 is readily removable from the housing 12 and a dental spray tool 24, shown in FIG. 7 can be mounted with the housing 12 in its place, as shown in FIG. 6.

With the dental brush tool 22 fitted to the housing 12 as appears in FIGS. 1 and 2, the appliance 10 can rotate bristle tufts 26 and 28 of the tool 22 by way of reciprocating rods 30 and 32 that project from the housing 12 beyond the tool mount 20 and are driven by the motor 14 by way of the reciprocating drive mechanism 16. The illustrated appliance rotates one set of bristle tufts 26 of the tool 22 clockwise and at the same time rotate another set of bristle tufts 28 counterclockwise and repeatedly reverses the counter-rotation.

The appliance 10 in addition can pump a dentifrice or similar liquid from the pump mechanism 18 to the dental brush tool 22, for discharge to the dental site being brushed. The motor 14 drives the pump mechanism 18 concurrently with the drive of the reciprocating drive mechanism 16.

When the dental spray tool 24 is fitted to the appliance housing 12, as shown in FIG. 6, the same motor 14 drives the pump mechanism 18 by way of the drive mechanism 16, to deliver a selected dentifrice liquid to the spray tool 24, for discharge to a dental site.

The dental appliance 10 thus has a single motorized powered handle-forming housing 12 that drivingly mounts either a dental brush tool 22 or a dental spray tool 24. The motorized housing 12 can deliver or discharge, by way of the tool a selected liquid appropriate for whatever tool is in place.

With reference to FIGS. 1 and 2, the illustrated tool has an on/off switch 34 at the axial end opposite the tool mount 20. A diverter switch 36 is mounted on the housing 12 for selecting which liquid is to be delivered to the pump mechanism 18. In particular the illustrated appliance 10 is connected with a reservoir 38 of a dentifrice liquid and of a spray liquid by way of a twin-passage conduit 40 that feeds into the housing 12 to the selector switch 36, form which a single conduit 41 feeds to the pump mechanism 18.

The illustrated appliance housing 12 is generally cylindrical in shape and elongated along an axis 42; the appliance has arranged in axial succession the switch 34, the motor 14, the reciprocating drive mechanism 16, the pump mechanism 18, the tool mount 20, and the extensions of the reciprocating rods 30 and 32 that pass within the dental brush tool to drive the axial succession of bristle tufts 26 and 28. The motor 14, which can be powered either by batteries mounted within the housing 14 or from an external power source, has an output shaft 14a centered on the axis 42 and mechanically coupled to rotate a beveled gear 44 about the axis 42. The beveled gear 44 is drivingly engaged with a pair of cranking bevel gears 46 and 48. The cranking gears 46 and 48 are rotatable about a common axis 50, perpendicular to the axis 42, by way of shaft screws that mount each gear to a support frame 54 that in turn is seated within the housing 12. The cranking gears 46 and 48 are spaced apart along the axis 50, as appears in FIG. 1. A crank rod 56 is pinned to the periphery of the cranking gear 46 and a similar crank rod 58 is pinned to the cranking gear 48. Each crank rod 56 and 58 extends generally along the direction of axis 42 and is rotatably fastened at its end remote from its respective cranking gear to one reciprocating rod 30 and 32, respectively.

As shown in FIGS. 1, 2, and 5, the reciprocating rods extend side-by-side along the direction of axis 42 and are axially slidable relative to the housing 12.

With this construction, rotation of the motor 14 rotatably drives the input bevel gear 44 to impart oppositely-directed rotations to the cranking gears 46 and 48. These oppositely directed rotations drive the crank rods 56 and 58 to reciprocate back and forth. The crank rods are coupled to diametrically opposite sides of the two cranking gears and thus move 180° out of phase. The crank rods thereby reciprocatingly drive the rods 30 and 32 back and forth, with an out-of-phase motion, parallel to the axis 42.

FIGS. 1 and 2 show that each reciprocating rod 30 and 32 has, at its axially far end, a flat gear 60, 62 respectively, arranged essentially as an axial extension of the corresponding rod 30, 32. Each flat gear 60, 62 is drivingly engaged with one set of brush tool bristle elements 26 and 28. More particularly, the illustrated dental brush tool 22 has a body 70 that is elongated along the axis 42. The tool has a mount 72 at one axial end that mating engages the housing mount 20 and that is arranged in axial succession with a neck portion 74 and a brush head 76. The tool body 70 has an axial hollow passageway into which the reciprocating rods 30 and 32 extend to dispose the flat gears 60 and 62 within the tool brush head 76.

Each illustrated bristle tuft 26, 28 has, as shown in FIGS. 1 and 2, a geared mounting base 78 that is secured in the brush head 76, with the bristles 78a thereof extending parallel and side-by-side to the bristles 78a of other tufts 26 and 28. The bristle tufts 26 are arranged essentially in lineal succession along the axis 42, with a spur gear 78b on each mounting base engaged with and in the same plane as the spur gear 78b of other ones of the bristle tufts 26. One bristle tuft 26 in the set thereof has a further spur gear 78c axially spaced from and concentric with the spur gear 78b thereof and drivingly engaged with the flat gear 60.

The illustrated bristle tufts 28 are similarly constructed and arranged, with one spur gear 78c of that set of bristle tufts drivingly engaged with the flat gear 62.

With this construction, the reciprocating drive that the motor 14 imparts to the flat gears 60 and 62 rotatingly drives one set of bristle tufts 26 clockwise while driving the other set bristle tufts 28 counterclockwise, and repeatedly reverses the driving directions as the cranking gears 46 and 48 rotate.

In addition to driving the bristle tufts 26 and 28 rotatably with reversed and opposite rotation directions, the motor 14 and reciprocating drive mechanism 16 pumps a dentifrice liquid by way of the pump mechanism 18 for discharge from the brush tool head 76. More particularly, the pump mechanism 18 in the housing 12 forms a pair of side-by-side pump of chambers 82 and 84 within an internal passage of the housing 12 and separated from one another by the back ends (right-most in FIG. 1) of the reciprocating rods 30 and 32. In the illustrated appliance, each reciprocating rod 30 and 32 has an enlarged end that links with the mating cranking rod 56, 58 and which forms a piston 86, 88 respectively slidably seated within one cylinder chamber 82, 84.

As shown in FIG. 1, liquid from the reservoir 38, as selected by the selector switch 36, is directed within the housing 12 from the conduit 41 to a pump inlet port 90 and then to an inlet valve 92 that is coupled by a passage 94 with the pump chamber 84. An outlet valve 96 feeds from the axially forward end (left-most in FIG. 1) of chamber 84 to an axially extending port 98 at the tool mount 20.

The dental brush tool 22 has an internal liquid passage 100 that feeds from the tool mount 72, which is coupled with the housing port 98, along the tool neck 74 to the brush head 76. The (illustrated) passage 100 is apertured at spaced intervals along the brush head 76, at locations adjacent to the bristle tufts 26, 28, for the distributed discharge of liquid at the same dental site with which the bristle tufts are engaged.

As also shown in FIGS. 1 and 2, the pump mechanism 18 has a preferably identical arrangement of an inlet valve 102 that feeds liquid from the selector switch 36 to the pump chamber 82, and has an outlet valve 104 and port 105 for controlling the delivery of pumped liquid from that chamber to whatever dental tool in attached to the appliance housing 12 by way of the mount 20.

A separate branch of the passage 100 fees in the brush tool from the coupling with the pump outlet valve 104 to discharge apertures adjacent the bristle tufts 26.

The illustrated tool mount 20 of the appliance 10 has, as shown in FIGS. 1 and 2, a mounting stem 106 axially projection on the housing beyond an annular surface 108. The stem has a flat axially end face 110 beyond which the reciprocating rods 30 and 32 extend. Each outlet ports 98 and 105 forms, in the illustrated mount, an hydraulic coupling receptacle that opens to the end face 106.

The mount 72 of the illustrated dental brush tool 22 has a flat end face 118 axially recessed with a socket-like recess 120. When the tool 22 is joined to the appliance housing 12 as shown in FIGS. 1 and 2, the socket recess 120 matingly receives the housing stem 106 and the tool end face 118 is closely adjacent to the housing end face 108.

A central axial passage 122 extends within the tool body from the socket recess 120 along the length of the neck 74 to within the brush head 76, for receiving the reciprocating rods 30 and 32 and the flat gears 60 and 62 which they carry. The illustrated tool mount 72 further has hydraulic coupling plugs 124 and 126 that project axially into the socket recess 120, from the flat end of the recess, for matingly (telescopically) interfitting with the hydraulic receptors at the ports 98 and 105 respectively.

With this structure of the housing mount 20 and the mating tool mount 72, the brush tool 22 is removably and replaceably mountable with the appliance housing 12. When the tool is attached, it moves with the housing essentially as a unit, and the reciprocating drive developed with the drive mechanism 16 rotatingly drives the bristle tufts 26 and 28. Further, the hydraulic coupling receptacles mate with the plugs 124 and 126 for the delivery of liquid dentrifice from the pump mechanism 18, for discharge at the brush tool head 76. The housing mount 20 preferably includes seals, such as O-rings, at the hydraulic receptacle, as illustrated, and the mount can include a detent mechanism, all as conventional for removable and replaceable fittings of this type. The interfitting stem 106 and socket recess 120 can each have a circular cross-section and be keyed to interfit only with alignment of the coupling plugs with the receptacle; alternatively, the stem and recess can have mating and preferably polarized non-circular cross-sections, as those skilled in the art will understand from the foregoing disclosure.

Alternative to operating the dental brush tool 22, the powered housing 12 can operatively mount the dental spray tool 24. As shown in FIGS. 6 and 7, the spray tool has a mount 130 similar to the mount 72 of the brush tool with a socket like recess 132 and with hydraulic coupling plugs 134, 136 for removably and replaceably mountingly engaging with the housing stem 106 and the hydraulic coupling receptacles at ports 98 and 105, respectively. A hollow stem 138 on the spray tool leads from the mounting recess 132 to a spray nozzle 140. The two coupling plugs 134 and 136 are coupled with the hollow within the stem 138 for feeding liquid pumped into the coupling plugs from the housing pump mechanism 18 through the stem for discharge at the spray nozzle 140.

A dental appliance according to the features of this invention thus provides a user with a single powered handle that operates with a removable and replaceable dental brush tool and alternatively operates with a removable and replaceable dental jet spray tool. The powered handle houses a motor and a brush agitating mechanism together with a liquid dispensing pump mechanism, both operated by the single motor. The brush agitating mechanism couples with brush elements of the dental brush tool for agitating driving the brush elements. In the preferred illustrated embodiment, the drive mechanism rotates two sets of brush elements back and forth in opposite directions, and with the two sets being out of phase, i.e. rotating in opposite directions at any time. Concurrently the pump mechanism of the powered handle can deliver a liquid such as dentifrice for discharge by the dental brush tool to the dental site being cleaned or otherwise treated. When operating with the dental spray tool, the same pump mechanism of the powered handle can deliver a selected different liquid for discharge by the spray tool to a dental site.

The preferred brush agitating mechanism and liquid pumping mechanism described operates with a low level of vibration and otherwise is convenient to use owing to ease in switching between one liquid for the brush operation and another liquid for the spray operation and further owing to ease in changing between the brush tool and the spray tool.

It will thus be seen that the invention efficiently attains the objects set forth above, among those made apparent from the preceding description. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language might fall therebetween.

Having described the invention, what is claimed as new and secured by Letters Patent is:

1. Dental appliance apparatus comprising
    A. manually deployable housing means,
    B. power means mounted within said housing means, said power means including means for actuating brush elements of a dental brush tool and including means for controlling delivery of liquid to a dental tool,
    C. a first tool mount on said housing means for removably and replaceably mounting any one of a dental brush tool and a dental spray tool to said housing means,
    D. said dental brush tool having actuatable brush elements and having a second tool mount that couples removably and replaceably with said first tool mount for mounting said brush tool to said housing means operably coupled with said actuating means for actuating said brush elements for movement relative to the second tool mount, and
    E. said dental spray tool having a liquid-discharging spray element and having a third tool mount that couples removably and replaceably with said first tool mount for mounting said spray tool to said housing means alternative to said brush tool and operably coupled with said controlling means for the delivery to said spray element of liquid supplied to said power means.

2. Dental appliance apparatus according to claim 1 in which said power means includes pump means for delivering a dentifrice liquid to said brush tool and alternatively for delivering a spray liquid to said spray tool.

3. Dental appliance apparatus according to claim 2 in which said first tool mount is arranged for engaging each of said second tool mount and said third tool mount for providing both mechanical tool support and for coupling liquid from said pump means to said brush element of said brush tool and to said spray element of said spray tool.

4. In dental appliance apparatus having a manually deployable housing and having a motor element within said housing for providing reciprocating drive to drive actuable brush elements of a dental brush tool, the improvement comprising
- A. first and second side-by-side reciprocating members coupled with said motor element, for receiving out-of-phase reciprocating motion,
- B. means for operatively coupling said reciprocating members with said brush elements of said dental tool for actuating said brush elements,
- C. liquid pump means mounted within said housing and arranged for receiving liquid from a supply thereof, said pump means having at least first and second pumping chambers, each of which is slideably fitted with a pumping piston, and having valved fluid passages for the delivery of the received liquid to said chambers and for the further delivery of pumped liquid from said chambers for application to said dental tool,
- D. means operatively connecting said pump means with said motor element for reciprocating said piston elements relative to said chamber elements, and
- E. means operatively connecting said reciprocating members with said motor element for the driving reciprocation both of said pump means and of said reciprocating members in common by said motor element.

5. In dental appliance apparatus according to claim 4, the further improvement in which
- A. said brush tool comprises plural first and second brush elements, each rotatably mounted with said brush tool,
- B. said first reciprocating member is coupled with at least one first brush element for agitatingly driving said first brush elements, and
- C. said second reciprocating member is coupled with at least one second brush element for agitatingly driving said second brush elements.

* * * * *